(12) United States Patent
Laghi et al.

(10) Patent No.: US 9,364,347 B2
(45) Date of Patent: Jun. 14, 2016

(54) POCKETED DOUBLE FABRIC PROSTHETIC LINER

(76) Inventors: Aldo A. Laghi, Clearwater, FL (US); Ronald A. Christaldi, Tampa, FL (US)

(*) Notice: Subject to any disclaimer, the term of this patent is extended or adjusted under 35 U.S.C. 154(b) by 271 days.

(21) Appl. No.: 13/419,315

(22) Filed: Mar. 13, 2012

(65) Prior Publication Data

US 2013/0245786 A1    Sep. 19, 2013

(51) Int. Cl.
*A61F 2/78*    (2006.01)

(52) U.S. Cl.
CPC .......... *A61F 2/7812* (2013.01); *A61F 2002/785* (2013.01)

(58) Field of Classification Search
CPC .......................... A61F 2/7812; A61F 2002/785
USPC ............................................................. 623/36
See application file for complete search history.

(56) References Cited

U.S. PATENT DOCUMENTS

| | | | |
|---|---|---|---|
| 1,319,637 A | 10/1919 | Blevens | |
| 5,376,130 A * | 12/1994 | Courtney | 623/33 |
| 6,149,691 A | 11/2000 | Fay et al. | |
| 6,454,812 B1 * | 9/2002 | Laghi | 623/36 |
| 6,923,834 B2 | 8/2005 | Karason | |
| 7,291,182 B1 * | 11/2007 | Kania | 623/36 |
| 2002/0002405 A1 * | 1/2002 | Janusson et al. | 623/36 |
| 2002/0183859 A1 * | 12/2002 | Houser | 623/36 |
| 2004/0059432 A1 * | 3/2004 | Janusson et al. | 623/36 |
| 2005/0101693 A1 | 5/2005 | Arbogast et al. | |
| 2009/0036999 A1 * | 2/2009 | Egilsson et al. | 623/36 |
| 2010/0274364 A1 * | 10/2010 | Pacanowsky et al. | 623/36 |
| 2011/0270414 A1 | 11/2011 | Laghi et al. | |

* cited by examiner

*Primary Examiner* — Bruce E Snow
*Assistant Examiner* — Melissa Hoban (57) ABSTRACT

A prosthetic liner having a base elastic fabric layer impregnated with cushioning material on an interior surface of the base fabric layer and having one or more additional elastic fabric layers secured to and overlapping the base fabric layer to form pockets for introducing and retaining various types of padding selected by the user.

61 Claims, 10 Drawing Sheets

POCKETED DOUBLE FABRIC PROSTHETIC LINER

TECHNICAL FIELD

The present invention relates generally to a gel cushioned liner to be worn over an amputee's residual limb regardless of the amputation being a leg amputation below-the-knee, BTK, or above-the-knee, ATK, or and arm amputation below-the-elbow, BTE, or above-the-elbow, ATE, and more particularly to a gel cushioned liner having multiple outer fabric layers attached together to form pockets for retaining padding in selected locations within the liner.

BACKGROUND

The term "Prosthetic Liner" is used to describe any of many various "sock-like" medical devices worn by amputees to protect their residual limb. Although the majority of the following disclosure describes the prosthetic liner in terms of a leg amputation, the present invention is not intended to be limited to leg amputations and also finds practical applications to other prostheses such as for an arm amputation. The liner is often worn directly over the residual limb of the amputee, and consists of a soft interfacing material (Gel, Silicone, Polyurethane) affixed to a more durable outer layer (often fabric constructed of Nylon or Polyester). The traditional process generally involves either one or two pieces of shaped fabric that are sewn together on all sides except the top to form a proximal open-end tubular-shaped fabric member or tubular "sock". The tubular-shaped fabric is then often placed into an injection molding machine and coated with hot gel or silicone that adheres to the inside surface of the tubular fabric to form the soft inner layer. The purpose of the liner is to provide both comfort to the residual limb of the amputee, and to allow the residual limb to slide into (and fit comfortably once inside) a molded prosthetic socket. Such liners commonly come in two styles: cushion liners for suction suspensions, and liners with threaded distal encapsulations for lock and pin suspension systems. A brief search of the Prosthetics Industry will show that these styles of prosthetic liners have been the preferred style of liner over the last several decades.

When the amputee uses a prosthetic device, the amputee simply attaches a prosthetic limb to their residual limb by means of a rigid socket, liner, and a suspension means. The rigid socket can be custom fabricated to match the shape of the intended user's residual limb and can be formed from a variety of different materials, including but not limited to thermoplastic materials, fiber-reinforced thermoset materials, as well as woods and metals. Because the residual limb interfaces with the hard, rigid prosthetic limb, this interface can become an area of discomfort over time since this interface is a load bearing interface between the residual limb and the prosthetic limb. In order to alleviate this discomfort and provide a degree of cushioning to lessen the impact of the load, prosthetic liners are used as interface members between the hard prosthetic socket and the residual limb in order to increase comfort.

The more recent preferred style of liner such as that disclosed in U.S. Patent Application Publication 2011/0270414 A1, incorporated herein by reference, consists of an inner layer of gel, silicone, or polyurethane material that adheres to an outer layer of fabric. One method of manufacturing this traditional liner involves taking two separate pieces of identical die cut fabric and sewing them together on all sides, excluding the top, to form an integral open proximal ended tubular piece of fabric. This open proximal ended fabric "sock" is then placed in a molding apparatus and injection molded with a hot gel polymer, which bonds to the inside of the outer fabric, to form one version of the modern standard of liners noted above. This version of the standard liner has stitching running all the way around the liner that divides the liner into two distinct sides, i.e., an anterior side and a posterior side with the stitching extending along the sides of the residual limb when worn.

Although the present invention is illustrated and disclosed herein as having two distinctive sides, i. e., anterior and posterior sides, it is not intended to be limited as such. For example, the two distinctive sides of the liner could be disposed on the left and right sides of the residual limb when worn with the stitching residing along the anterior and posterior sides of the limb. Also, the present invention may have more than two distinctive fabric layers such as three or four or even five pieces of die cut fabric sewn together on all sides, excluding the top, to form an integral open proximal ended tubular piece of fabric. Furthermore, the pieces of fabric do not have to be identical and could be customized according to an amputee's needs.

Most of the available cushioned residuum prosthetic liners that are currently available have a tubular or conical construction. While intended to provide the best fit to the residual limb, at times they cannot provide the best form fit of the amputee's residuum since the residuum stump typically does not contain a completely uniform shape. For example, while a residuum stump generally may have a conical shape, the residuum stump will often have recessed areas in certain locations. A stump may generally have a conical or cubical shape with invariably recessed areas on, e.g., the medial side of the prominent tibia bone. Generally, for a BTK amputee, the left side residual limb will have the recessed area predominantly on the right side of the tibia bone. There is also typically a smaller recessed area on the left side. On the right side residual limb, the predominant recessed area is on the left side of the tibia bone, with smaller recessed areas on the right side. Usually the greatest recess occurs immediately below the patella, on either side. In addition, left side amputees typically have a right side bias to the bony prominence of the below knee stump, and right side amputees have a similar bias to the left side. Unfortunately, there are also recesses formed in the residual limb caused by injury. Conventional tubular or conical elastic liners simply cannot account for these several variable conditions without using extremely high levels of elastic tension which compress the outer-most points along the stump's circumference, causing discomfort and a non-uniform fit. Conventional prosthetic liners do not accommodate the non-uniform nature of the residuum and this can result in the amputee experiencing wearing discomfort due to the non-uniform fit.

Furthermore, many amputees experience a swelling of the stump. When the residuum is in a prosthetic socket the stump tends to contract significantly, and when taken out of the socket the stump tends to expand within minutes of removal. This expansion and contraction of the residuum contributes to the development of air pockets and the generation of obtrusive noises since a liner which may have provided a comfortable fit on the expanded stump becomes a loose fit with air pocket opportunities when the residuum is placed inside the prosthetic socket. In addition, and over time, an amputee's residuum tends to adjust in size, usually shrinking. As these changes occur they increase the tendency for the pistoning effect, described above, to occur. In addition to the embarrassment caused by the sound effects generated by pistoning, cushioned socks which allow or promote air pocket formation quickly wear out and, if not replaced often, lead to lesions, etc. on the residuum.

Maximum comfort is critical component to the amputee (and consequentially, to their prosthetist) during their search for the correct prosthetic liner. As such, many different manufacturing features can be added or altered in order to enhance the basic liner concept highlighted above. For instance, as disclosed in U.S. Patent Application Publication 2011/0270414 A1, the stretch and thickness characteristics of the external fabric are often altered to allow greater ranges of motion for varying parts of the residual limb. As disclosed in U.S. Patent Application Publication 2005/0101693 A1, incorporated herein by reference, the thicknesses of the internal layer can be altered by tapering or adding extra padding to sensitive skin areas, while reducing bulk and un-necessary material and weight in other areas. It is well established in the marketplace that gel strips or foam padding are often attempted to be added to the outside of the prosthetic liner (between the liner and the socket) to make up for volume fluctuations in the residual limb of the amputee that occur throughout the course of the day, or to make up for an ill-fitting permanent prosthesis. Items designed to serve these functions have been available for years, but the inherent difficulty lies in affixing them to the outside of the traditional liner and having them remain in this intended position inside the socket over the duration of the normal usage period. As disclosed in U.S. Pat. Nos. 6,149,691 and 6,923,834, foam or pneumatic padding is often added to the socket to improve the fit in the case of amputees not being fitted correctly into their socket. As disclosed in U.S. Pat. No. 1,319,637, the prosthetic liner includes a series of woven or knitted stump socks secured to each other at their distal ends. Each layer is adapted to be rolled upon the residual limb to provide pockets for receiving padding between the layers.

Although the above discussed prior art devices are intended to enhance comfort for the user, they do have drawbacks. Either the padding is molded into the existing material during manufacture, or adhered to existing surfaces of the liner or socket or both, or permanently disposed between layers of the liners. Although the last prior art device mentioned does have an elastic pad disposed between the fabric layers, the pad must be held to the inner layer before the outer layer is rolled up and over the pad to hold it in place which is a complex operation with no guarantees that the pad will remain in the desired position.

Thus, there is still a need in the art for a prosthetic liner which overcomes the deficiencies of the prior art and is constructed so that padding could be easily inserted into or removed from the liner with minimal effort on the part of the wearer. This need is not only limited to comfort padding, but extends to other therapeutic applications such as heat therapy as is discussed hereinafter. The "pocket(s)" created by the additional layer(s) of fabric in the present invention provide enormous potential to the end user.

BRIEF SUMMARY OF THE INVENTION

The liner of the present invention is directly related to an improvement over the aforementioned liners having two external elastic fabric layers, which for clarity purposes will be referred to hereinafter as "base fabric layers". Instead of simply using only the two base elastic fabric layers, one or more additional elastic fabric layers overlapping the base fabric layers are utilized to create the "sock" portion of the liner. After molding of this tubular "sock", the end result is an otherwise traditional liner, with the improvement of one or more additional layers of elastic fabric overlapping one or more of the base elastic fabric layers. The additional fabric layers together with the base fabric layers on the outside of the liner create "pockets" between the base fabric layer and the one or more additional layers. Within the pockets, an amputee may selectively insert or remove various types of padding depending on the needs of the individual such as foam or pneumatic padding for comfort or heating padding to enhance blood flow. These pockets may be disposed either on one or both the posterior and anterior side of the prosthetic liner or on the left or right sides of the residual limb depending on the needs of the user. Also, in the case where more than two identically or non-identically cut base fabrics are used and depending on how many of the base fabrics are provided with overlapping additional fabric layers, the pockets may be disposed around the residual limb as needed. Immediate benefits, such as reduction of shear forces, increased durability, and increased ease of molding, all attest to the novelty of the present invention. Equally as important to the uniqueness of the present invention is the fact that the extra layer of elastic fabric (and associated pocket[s]) can be used by itself, i.e., without padding, with little if no difference from a liner having only a single base elastic fabric layer, but also can easily be used to incorporate additional features into the manufactured liner such as adding padding for comfort or heat padding to promote blood flow in the residual limb. The following sections will first describe the claimed invention in more detail followed by specific instances in which the present invention will serve the manufacturer by allowing the integration of additional properties or features into prosthetic liner products.

BRIEF DESCRIPTION OF THE DRAWINGS

In conjunction with the above described features, the present invention is more apparent from the following descriptions of the drawings and embodiments, wherein like reference numerals identify the same or equivalent features throughout the several views.

DETAILED DESCRIPTION OF THE PREFERRED EMBODIMENTS

Figure 1:
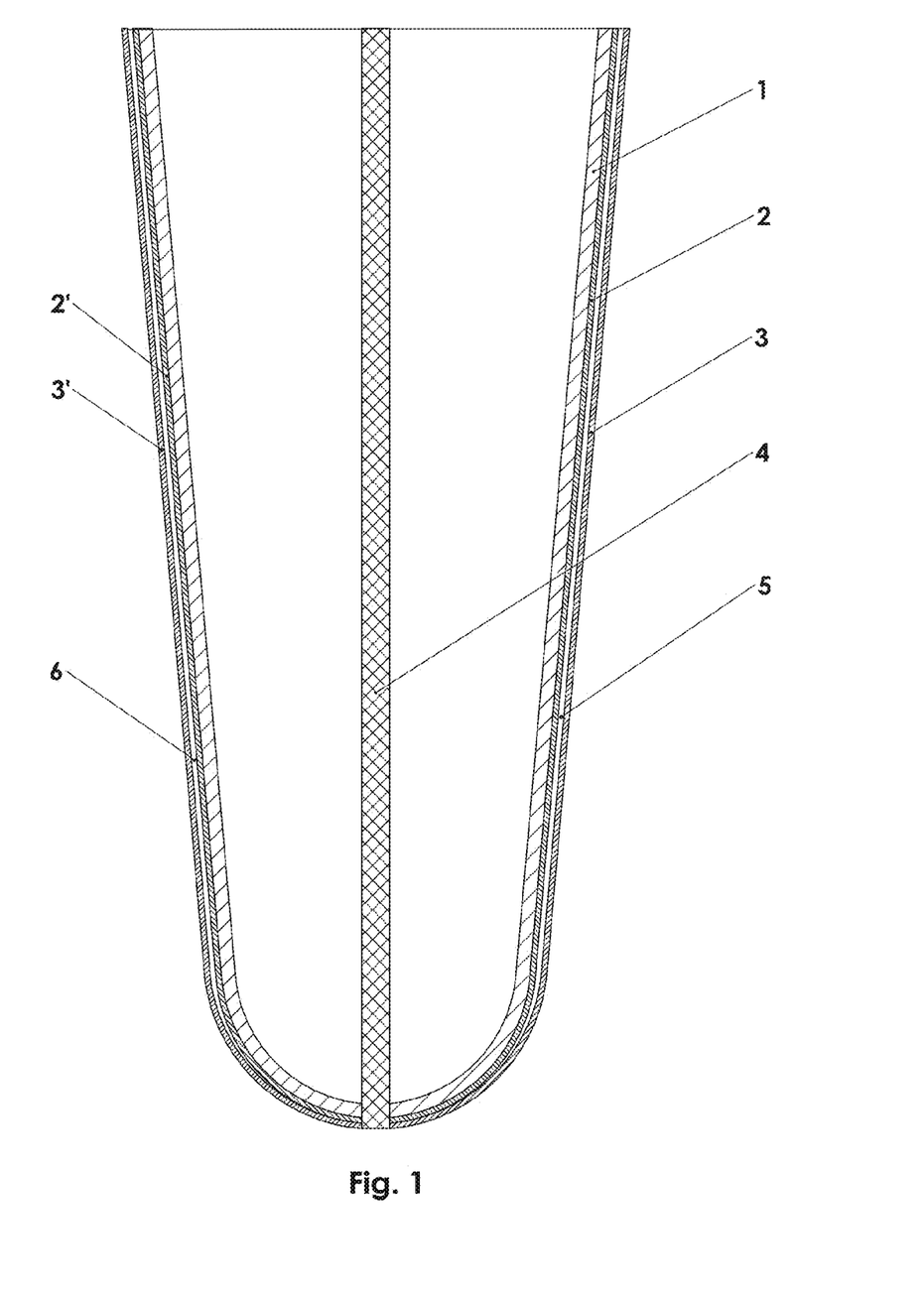
FIG. 1 is a side view of one embodiment of the present invention illustrating the pocket overlapping each base elastic fabric.

Referring to FIG. 1, a first embodiment of the present invention is illustrated. FIG. 1 exhibits the prosthetic liner with two identically sized die cut pieces of elastic fabric (2 and 2') having top and side edges. Fabrics (2 and 2') for purposes of description herein will be identified as "elastic base fabrics". The side edges only of the elastic base fabrics are attached to each other such as by stitching (4) forming a generally tubular sock-like shape having interior and exterior surfaces. A peel away fabric adhesive can be used during the sewing process to secure the sides of the fabric tubes together to ease the difficulty involved with stitching multiple pieces of fabric together at the same time. The interior surfaces are impregnated with a layer of cushioning material such as gel copolymer sold by ALPS, silicone or polyurethane. The resulting structure thus far described is similar to the "traditional" gel/silicone/polyurethane prosthetic liner presently available on the market. The elastic base fabrics in tubular form act to stabilize and cover the internal gel/silicone/polyurethane layer which exhibits stretch characteristics of 600%-200% and a Modulus of 50-500 psi. against the residual limb. It is critical to note that in addition to the proprietary ALPS Gel noted above, many different inner materials could be used, including but not limited to: silicone, thermoplastic elastomers (triblock), copolymer Styrenic gels, and polyurethane gels.

As discussed hereinabove, although the several embodiments of the present invention are illustrated to have two identical elastic base fabrics, they are not intended to be so limited. For example, there could be more than two identical die cut base fabrics, e.g., three, four or even five. The base fabrics do not have to be identical but could be of various shapes depending on the requirements of the user. Regardless of the number and shapes of the base fabrics, when attached together and impregnated with cushioning material on their interior surfaces, will form an open proximal ended, closed distal ended tubular sock-shaped liner into which a residual limb of an amputee can be introduced and used as a cushion layer interfacing the residual limb and the inside surface of a prosthetic socket. With the addition of outer layers of fabric over the elastic base fabrics provides an obvious level of enhanced durability over the traditional single-layered liner. The outer layers of fabric can also be used to reinforce, or to change the outer physical characteristics, of the inner tube of elastic base fabrics. The fabrics utilized would likely demonstrate longitudinal stretch characteristics of 5% to 180%, and transverse stretch characteristics of 50% to 250%., and could be between 0.30 mm and 1.5 mm in thickness. This could be specifically beneficial in the case that the manufacturer wanted to use a very thin (lightweight, low modulus, soft, aesthetically pleasing) fabric on both the inside and outside layer of the liner to achieve certain desirable end characteristics, but could not do so in the traditional processes due to the difficulties encountered when trying to injection mold a tube of very thin/fragile fabric. This new design can be used to give the manufacturer more lead-way in molding a wider array of fabric styles and thicknesses that have traditionally been too thin or too loosely knit to hold up to the process of injection molding. The simple addition of this fabric tube will also help to reduce the "shear forces" felt by the amputee during day to day activities. This extra fabric layer will act as an insulated buffer to help transfer these forces away from the most sensitive areas of the residual limb and disperse them more evenly across the entire surface area of the liner as a whole.

Referring again to FIG. 1, the novelty of the present invention lies in pockets (5) and (6) formed by the additional layers (3) and (3') of elastic fabric overlapping the base elastic fabrics. The additional layers (3) and (3') can be different than the base fabric layers, or different to each other, in composition, stretch characteristics, size and shape. For example, the additional layers could be polyester, or nylon, or rayon, etc. The pockets are formed by simultaneously attaching the side edges of the additional fabric layers to the side edges of the base fabric layers during the same sewing process used to make the tubular sock-shape liner. Once the interior surface of the base fabric layers are impregnated with the cushioning layer, the resulting liner, as shown, will have the additional fabric layers disposed in close overlapping relation to the base fabrics to define open proximal ended pockets, but will also be stretchable to open the pockets and allow the user to insert various types of padding as discussed hereinafter.

Although the preferred method of attaching the side edges of the fabric layers together is sewing, other well known methods could also be employed such as heat fusion, etc. It is further noted that the present invention could be used without any padding inserted into the pockets in the same manner as a traditional liner without any pockets.

Figure 2:
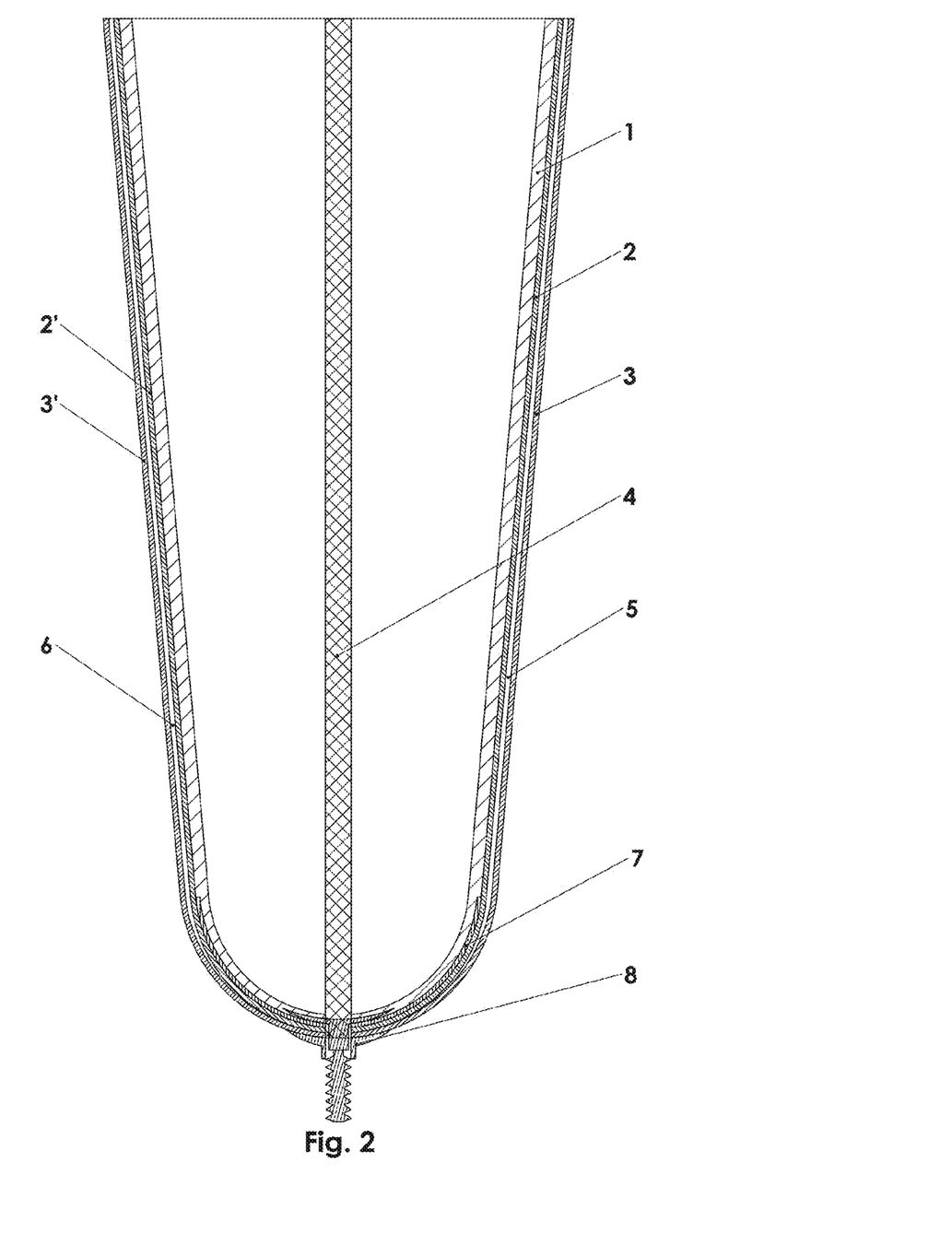
FIG. 2 is a side view similar to FIG. 1 and including a locking pin molded into the distal end of the liner.

The embodiment illustrated in FIG. 2 is similar to the embodiment of FIG. 1 with the addition of a distal insert (8) molded into the distal end of the liner for attaching a locking pin thereto.

Figure 3:
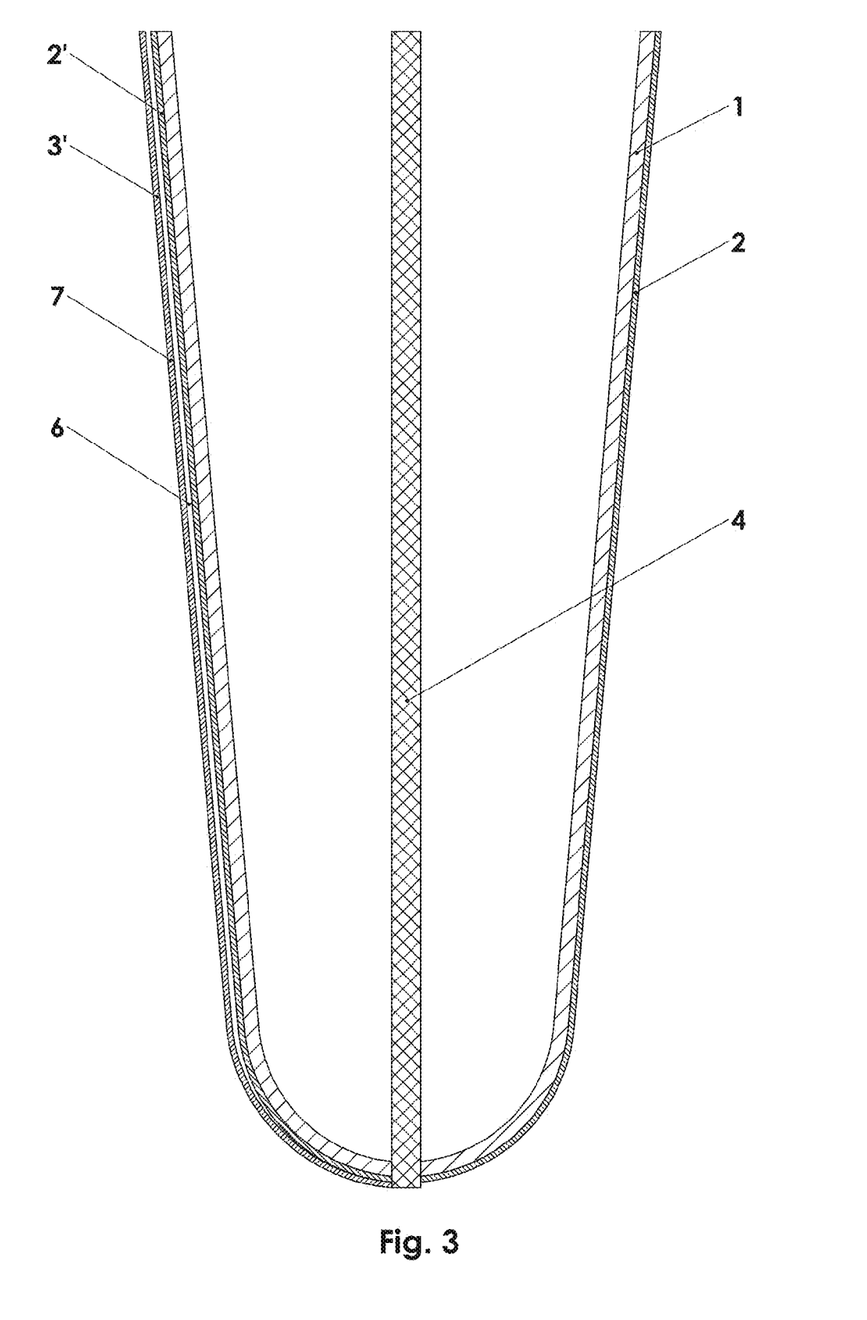
FIG. 3 is a side view of another embodiment of the present invention having only a single pocket.

Referring to FIG. 3, another embodiment of the present invention is illustrated to have only one pocket (6) formed by a single additional layer (3') overlapping base fabric layer (2'). Again, the size and shape of the fabric layers (2') and (3'), may be different from the base fabric layer (2).

Figure 4:
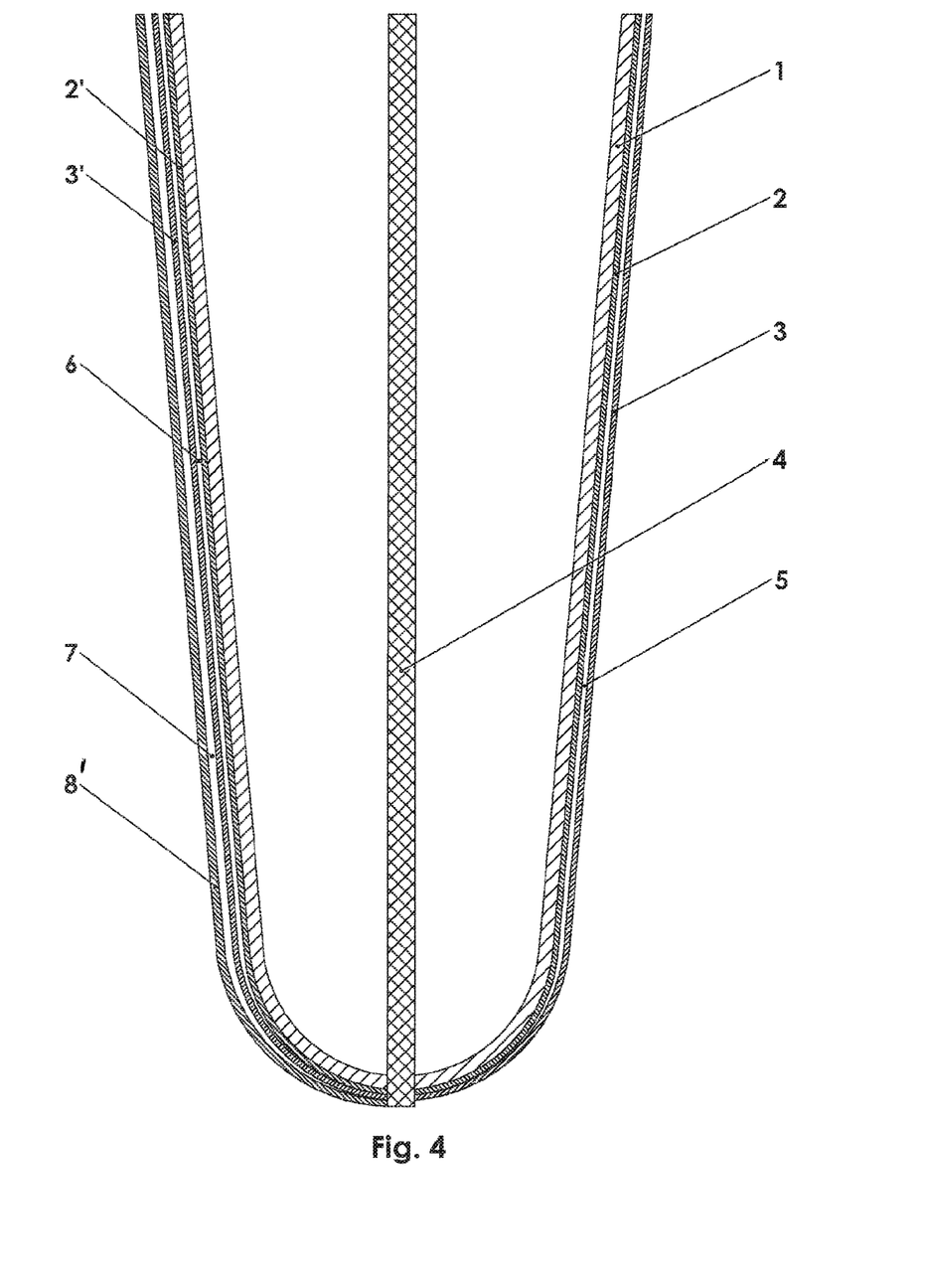
FIG. 4 is a side view of another embodiment of the present invention having one pocket on one side of the liner and two pockets on the opposite side of the liner.

Referring to FIG. 4, still another embodiment of the present invention is illustrated having three pockets (5), (6), and (7). Pockets (6) and (7) are formed by additional fabric layers (3') and (8') in the same manner as described above with respect to the embodiment illustrated in FIG. 1. Again, the number of pockets may depend on the requirements of the user. There may be two pockets formed on each base fabric. As mentioned above, there may be more than two base fabrics overlapped with one or more pockets.

Figure 5:
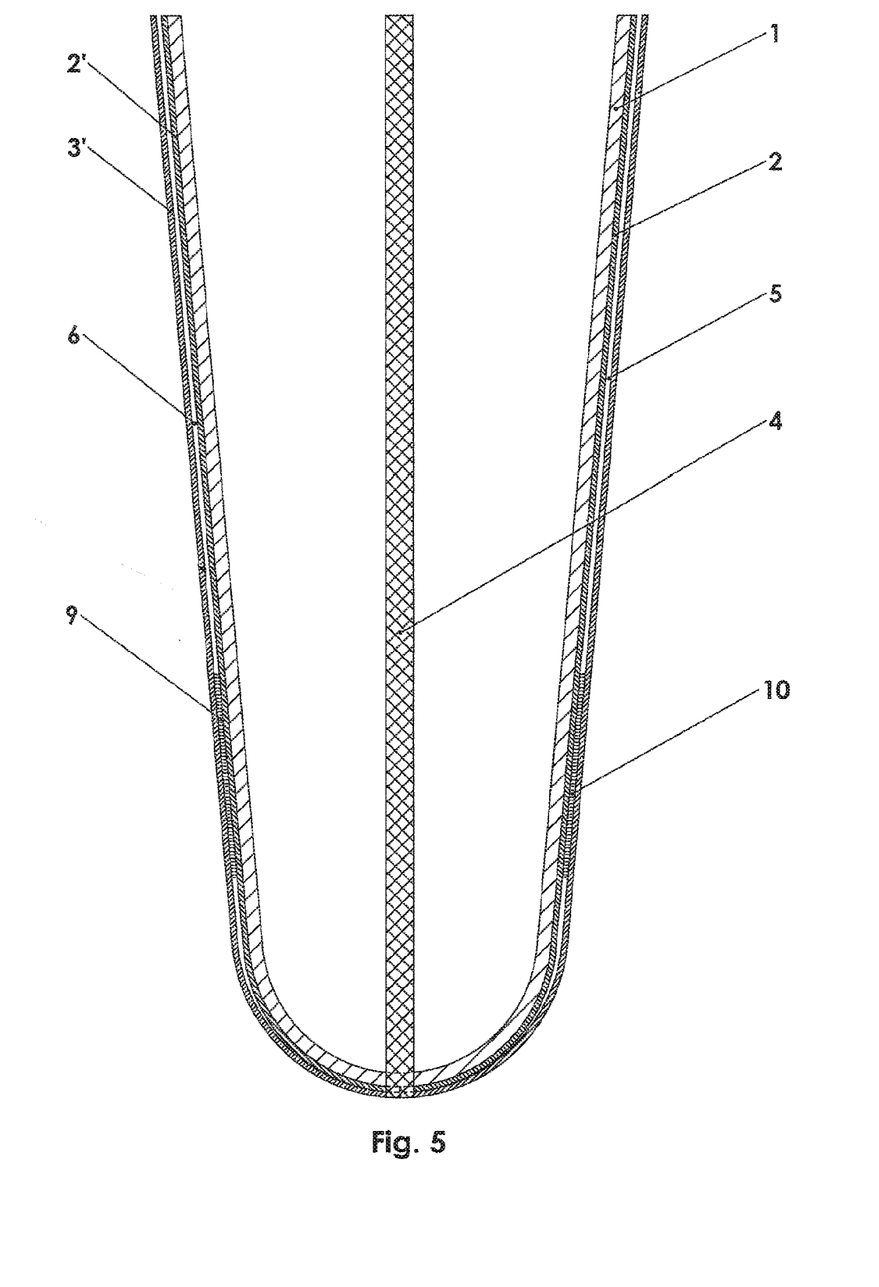
FIG. 5 is an embodiment similar to FIG. 1 including padding inserted into each pocket.

FIG. 5 is an embodiment like FIG. 1 showing how the open pockets can have padding inserted into the proximal open ends to possible locations (9) and (10) inside the pockets.

Figure 6:
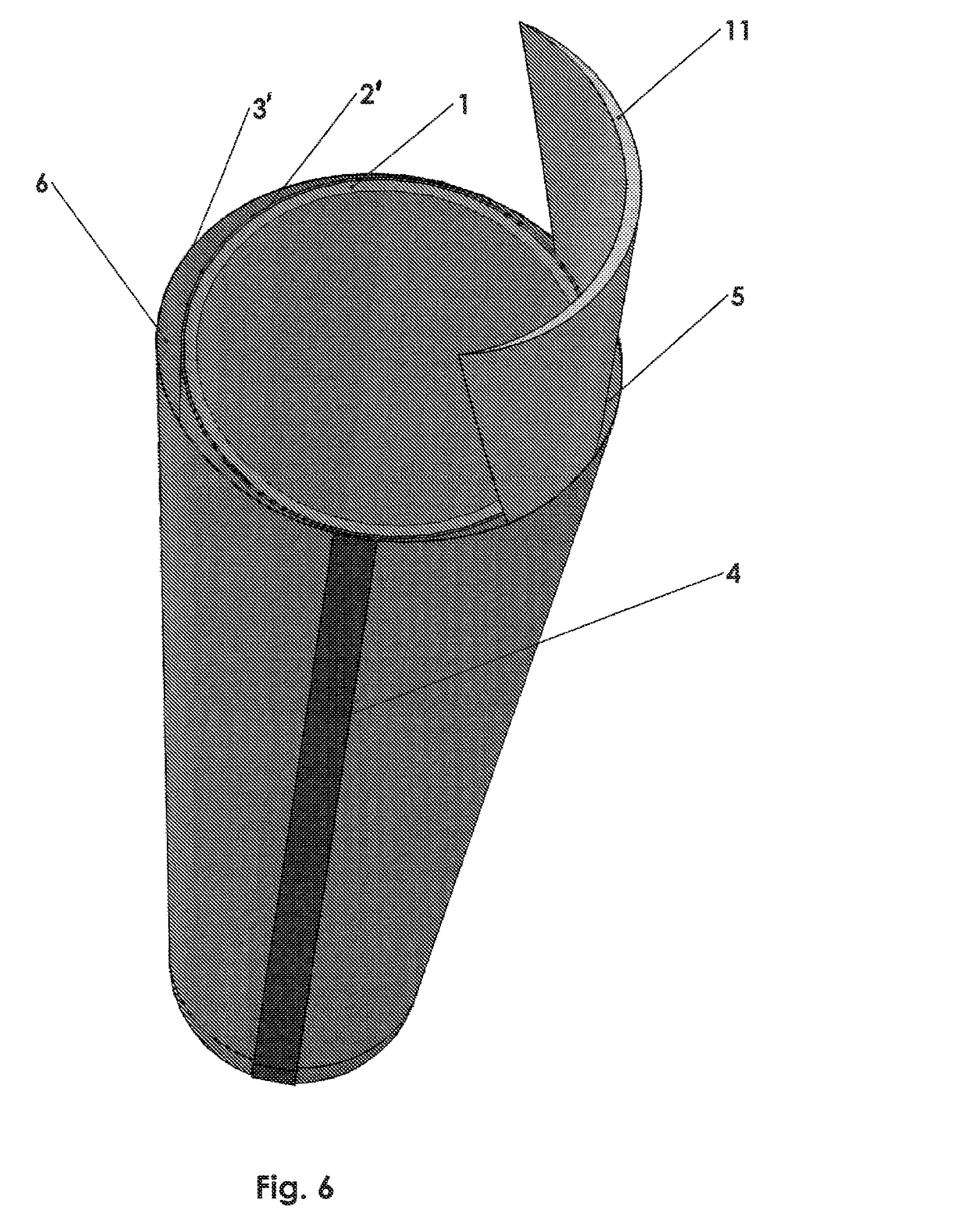
FIG. 6 is a graphical representation of the embodiment illustrated in FIG. 1 with foam padding partially inserted into on of the pockets.

FIG. 6 is a graphical representation similar to the embodiment of FIG. 1 showing how pockets can be opened to have padding (11) inserted into the proximal open ends of pockets (5 or 6).

Figure 7:
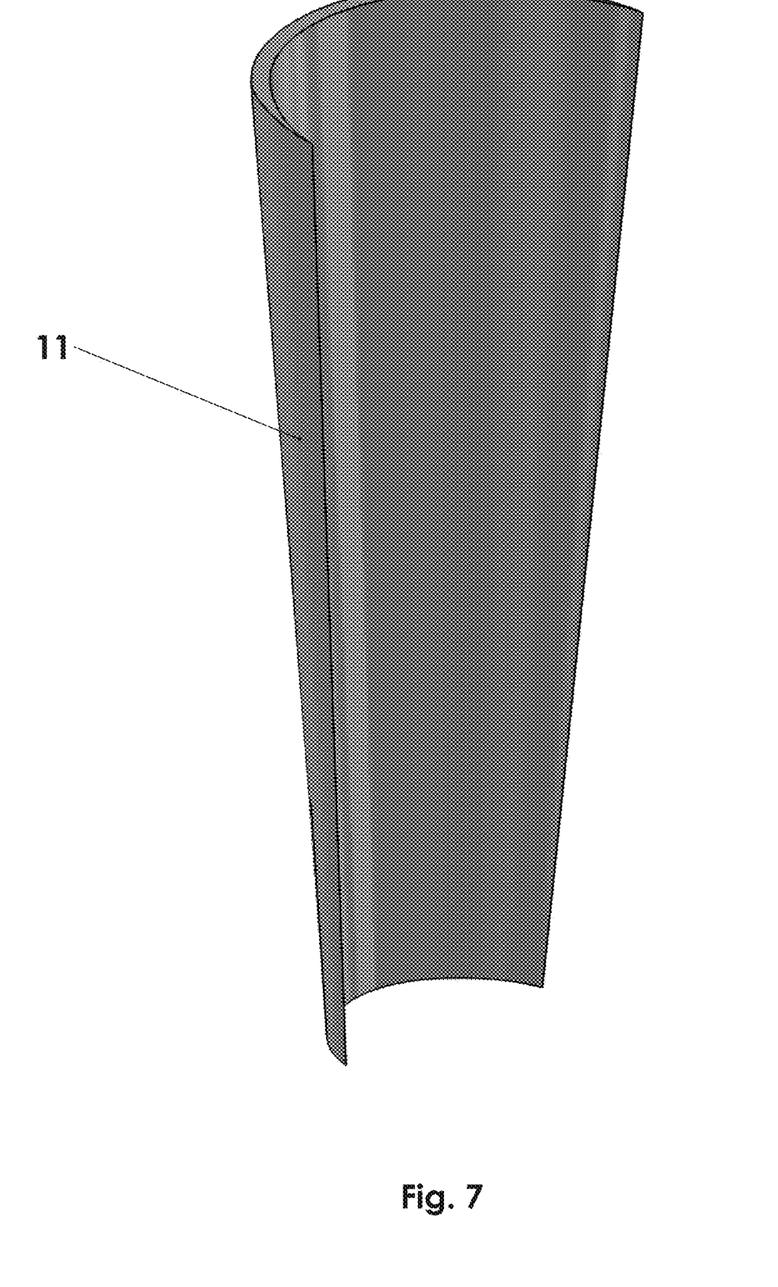
FIG. 7 is graphical representation of one type of padding adapted to be inserted into one of the pockets.
Figure 8:
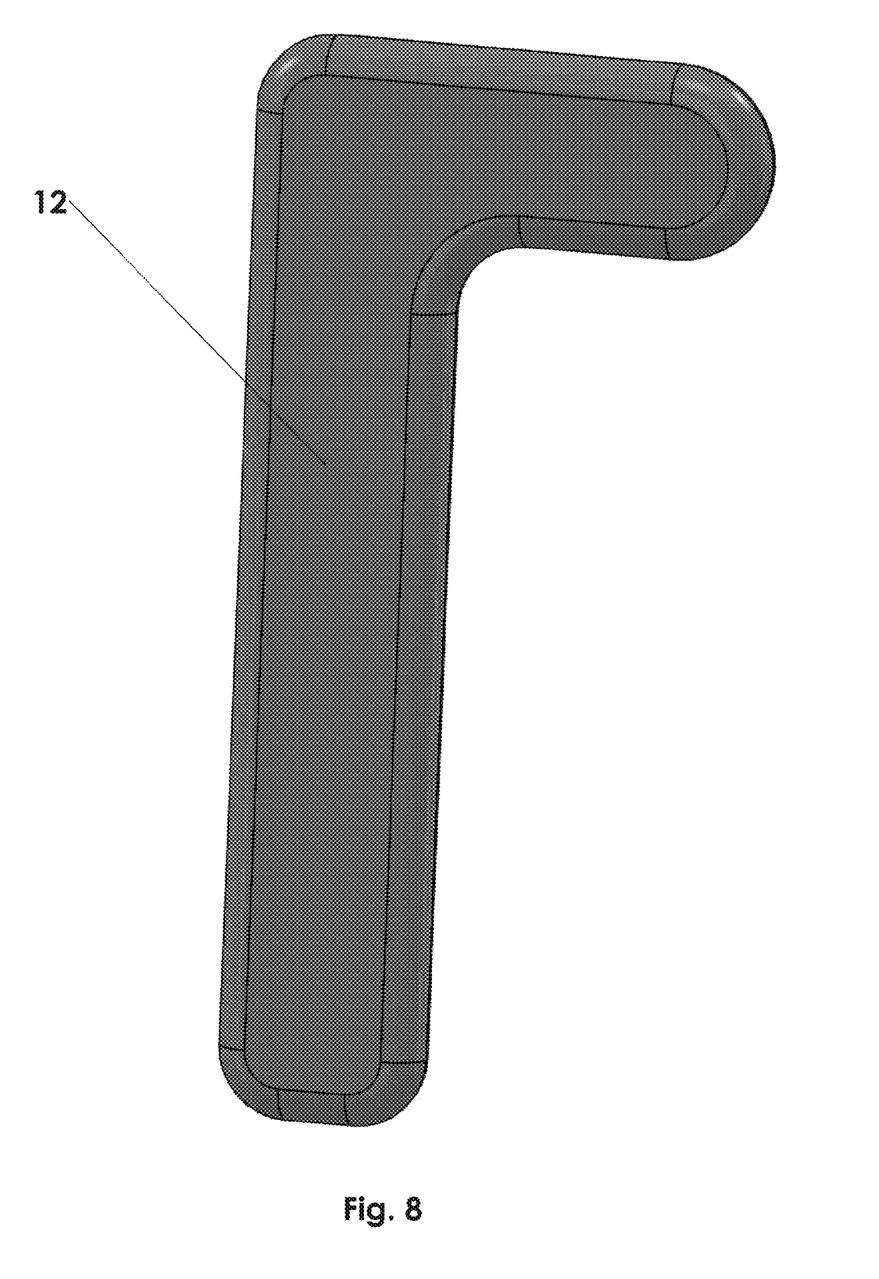
FIG. 8 is graphical representation of another type of padding adapted to be inserted into one of the pockets.

FIGS. 7 and 8 are graphical representations of two different types and shapes of padding that are usable with the liner of the present invention. Other types and shapes of padding such as foams, gels, pressure sensing films, heating pads, etc. may be custom made depending on the individual needs of the user that can easily be cut, fit, and tucked into the liner before the liner is inserted into the socket. Padding (11) shown in FIG. 7 may comprise a closed or open celled foam pad. Padding (12) shown in FIG. 8 may be open-celled foam with an impermeable outer skin, or an inflatable type pad. Again the shapes of the padding would depend on the shape of the projections and voids formed between the residual limb and inside surface of the socket.

The present invention is not only useful for providing comfort to the user but finds other utility as, for example, enhancing blood flow in a patient's extremities. It is well known that thermal treatment is useful in patients having poor blood flow caused by certain conditions such as diabetes. Such studies have been published such as *Skin Blood Flow in Diabetic Dermopathy* by Greg Wigington, B S; Binh Ngo, M D; Marc Rendell, M D in ARCH DERMATOL/VOL 140, October 2004, pp. 1248-1250; WWW.ARCHDERMATOL.COM and

*The Effect Of Local Temperature On Blood Flow In The Human Foot* by M. J. Allwood and H. S. Burry in J. Physiol. (1954) 1124, 345-357.

Figure 9:
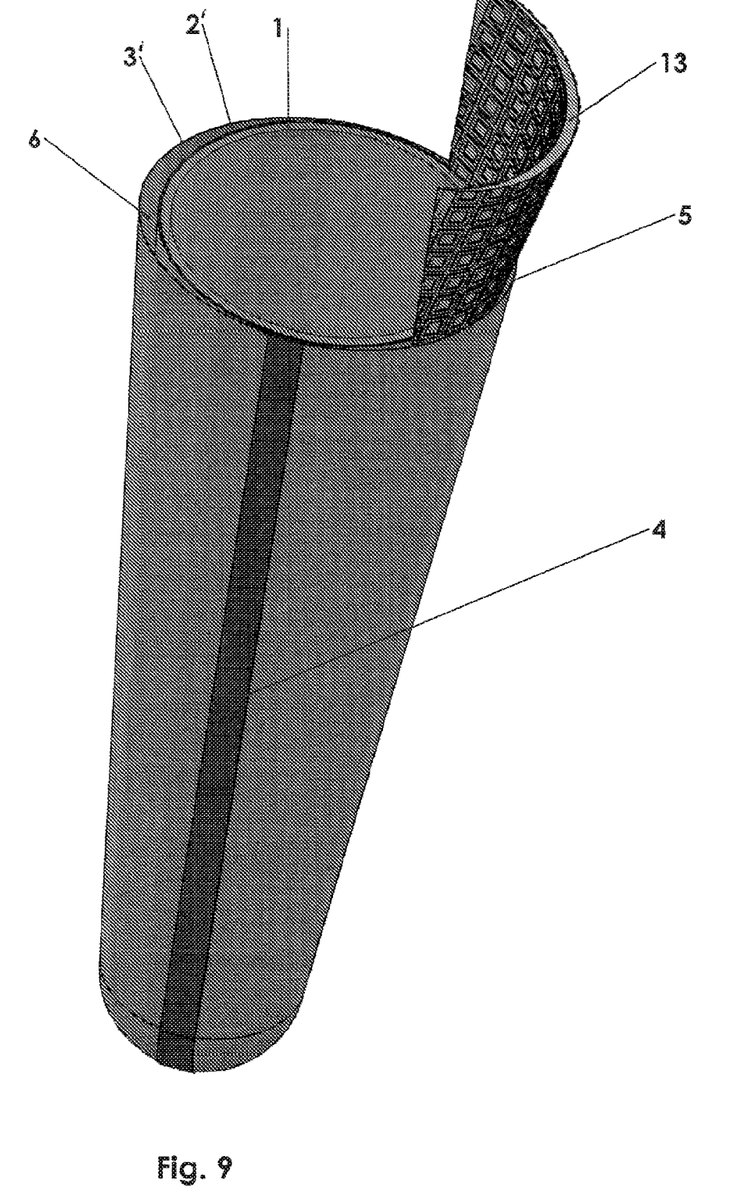
FIG. 9 is a graphical representation of the embodiment illustrated in FIG. 1 with heating padding partially inserted into one of the pockets.
Figure 10:
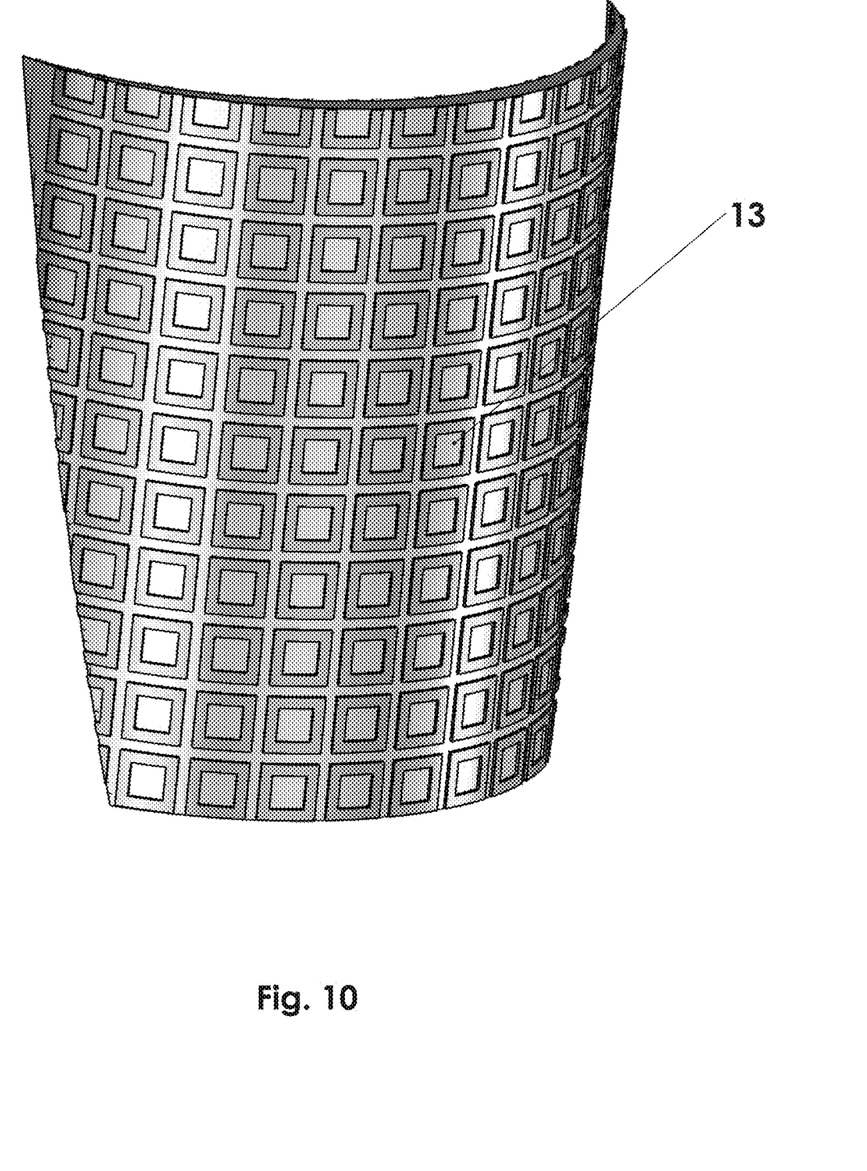
FIG. 10 is a rear view of the heating padding illustrated in FIG. 9.

Referring to FIGS. 9 and 10, the pocketed liner of the present invention is illustrated to have a heating padding 13 inserted into one of the pockets. Heating pad (13) is of the conventional type that could be preheated prior to being inserted into the pocket or could be of the type having battery operated electric resistant elements.

With this system, foams, gels, pressure sensing films, heating pads, etc. can be formed and custom-fit to easily retrofit poorly fitting sockets, or to provide additional benefits (see heat and Blood Circulation Survey), causing little or no additional bulk or thickness in unwanted areas.

The foregoing relates to the preferred exemplary embodiments of the invention, it being understood that other variants and embodiments thereof are possible within the spirit and scope of the invention, the latter being defined by the appended claims.

What is claimed is:

1. A cushion liner for enclosing an amputation stump comprising:
    an outer elastic fabric tubular-shaped covering having an open proximal end for introduction of said stump and a closed distal end opposite said open end, said outer elastic fabric tubular-shaped covering having an outer surface and an inner surface, a polymeric gel cushioning layer coated seamlessly on only said inner surface of said outer elastic fabric tubular-shaped covering that substantially conforms to the shape of said amputation stump when said liner is worn, said liner including at least a first pocket for receiving padding, said first pocket defined by at least a first stretchable elastic fabric panel separate from said outer elastic fabric tubular-shaped covering, said at least a first stretchable elastic fabric panel having a top edge and remaining side edges and wherein only said remaining side edges of said at least a first stretchable elastic fabric panel are attached to said outer surface of said outer elastic fabric tubular-shaped covering with said at least a first stretchable elastic fabric panel overlying said outer elastic fabric tubular-shaped covering, said top edge and portions of said at least a first stretchable elastic fabric panel extending within said attached remaining side edges are unattached to said outer elastic fabric tubular-shaped covering thereby permitting said top edge of said at least a first stretchable elastic fabric panel and portions of said at least a first stretchable elastic fabric panel extending within said attached remaining side edges to be stretched away from said outer elastic fabric tubular-shaped covering for inserting padding into said at least a first pocket.

2. A cushion liner as claimed in claim 1, wherein said cushion liner includes at least a second pocket, said second pocket defined by at least a second stretchable elastic fabric panel separate from said outer elastic fabric tubular-shaped covering, said at least a second stretchable elastic fabric panel having a top edge and remaining side edges and wherein only said remaining side edges of said at least a second stretchable elastic fabric panel are attached to said outer surface of said outer elastic fabric tubular-shaped covering with said at least a second stretchable elastic fabric panel overlying said outer elastic fabric tubular-shaped covering, said top edge and portions of said at least a second stretchable elastic fabric panel extending within said remaining attached side edges are unattached to said outer elastic fabric tubular-shaped covering thereby permitting said top edge of said at least a second stretchable elastic fabric panel and portions of said at least a second stretchable elastic fabric panel extending within said remaining attached side edges to be stretched away from said outer elastic fabric tubular-shaped covering for inserting padding into said at least a second pocket.

3. A cushion liner as claimed in claim 2, wherein said liner includes at least a third pocket, said at least a third pocket defined by at least a third stretchable elastic fabric panel separate from said outer elastic fabric tubular-shaped covering, said at least a first stretchable elastic fabric panel and said at least a second stretchable elastic fabric panel, said third stretchable elastic fabric panel having a top edge and remaining side edges and wherein only said remaining side edges of said third stretchable elastic fabric panel are attached to said at least a first stretchable elastic panel or to said at least a stretchable second elastic fabric panel with said at least a third stretchable elastic fabric panel overlying said at least a first stretchable elastic fabric panel or said at least a second stretchable elastic fabric panel whereby said top edge of said third stretchable elastic fabric panel and portions of said at least a third stretchable elastic fabric panel extending within said remaining attached side edges are unattached to said at least a first stretchable elastic fabric panel or to said at least a second stretchable elastic fabric panel thereby permitting said top edge of said at least a third stretchable elastic fabric panel and portions of said at least a third stretchable elastic fabric panel extending within said remaining attached side edges to be stretched away from said at least a first stretchable elastic fabric panel or said at least a second stretchable elastic fabric panel for inserting padding into said at least a third pocket.

4. A cushion liner as claimed in claim 3, wherein both said at least a third pocket and said overlapped first pocket or second pocket extend approximately from said proximal end to said distal end of said liner.

5. A cushion liner as claimed in claim 4, wherein said outer elastic fabric tubular-shaped covering and each of said elastic fabric panels have a longitudinal stretch of 5% to 180% and a transverse stretch of 50% to 250%.

6. A cushion liner as claimed in claim 5, wherein said outer elastic fabric tubular-shaped covering and each of said elastic fabric panels have a thickness of between 0.30 mm and 1.5mm.

7. A cushion liner as claimed in claim 4, wherein said outer elastic fabric tubular-shaped covering and each of said elastic fabric panels have a thickness of between 0.30 mm and 1.5 mm.

8. A cushion liner as claimed in claim 4, wherein said liner includes padding disposed in at least one of said pockets.

9. A cushion liner as claimed in claim 8, wherein said padding is a foam-type for comfort, a pneumatic-type for comfort, a heating-type for heat therapy or a pressure sensing type for sensing pressure points.

10. A cushion liner as claimed in claim 3, wherein said elastic fabric tubular-shaped covering and each of said stretchable elastic fabric panels are of the same material or of different materials.

11. A cushion liner as claimed in claim 10, wherein said outer elastic fabric tubular-shaped covering and each of said elastic fabric panels are polyester, rayon, nylon, or any combination thereof.

12. A cushion liner as claimed in claim 3, wherein said side edges of said at least a third stretchable elastic fabric panel is attached to said at least a first or second stretchable elastic fabric panel by sewing or heat fusion.

13. A cushion liner as claimed in claim 2, wherein said at least a second pocket extends approximately from said proximal end to said distal end of said liner.

14. A cushion liner as claimed in claim 2, wherein said side edges of said stretchable elastic fabric panels are attached to said outer elastic fabric tubular-shaped covering by sewing or heat fusion.

15. A cushion liner as claimed in claim 1, wherein said at least a first pocket extends approximately from said proximal end to said distal end of said liner.

16. A cushion liner as claimed in claim 1, wherein said polymeric cushioning material is a thermoplastic triblock copolymer, a copolymer styrene gel or a polyurethane gel.

17. A cushion liner as claimed in claim 1, wherein said liner includes a distal insert attached to the distal end of said liner.

18. A cushion liner as claimed in claim 17, wherein said distal insert is molded into said polymeric cushioning material at the distal end of said liner.

19. A cushion liner as claimed in claim 17, wherein said distal insert is attached to the outer surface of said outer elastic fabric tubular-shaped covering at the distal end of said liner.

20. A cushion liner as claimed in claim 1, wherein said outer elastic fabric tubular-shaped covering comprises at least two identically cut elastic fabric sheets each having a top edge and side edges wherein said side edges of each sheet are attached together to form said outer elastic fabric tubular-shaped covering having an open proximal end for introduction of said stump and a closed distal end opposite said open end, said at least two identically cut elastic fabric sheets each having an outer surface and an inner surface, said inner surfaces coated seamlessly with a polymeric cushioning material that substantially conforms to the shape of said amputation stump when said liner is worn.

21. A cushion liner as claimed in claim 20, wherein remaining side edges of said at least a first stretchable elastic fabric panel are attached to said side edges of one of said at least two identically cut elastic fabric sheets with said first stretchable elastic fabric panel overlying said one of said at least two identically cut elastic fabric sheets and with said top edge and portions of said at least a first stretchable elastic fabric panel extending within said attached remaining side edges being unattached to said one of said at least two identically cut elastic fabric sheets, thereby permitting said top edge of said at least a first stretchable elastic fabric panel and portions of said at least a first stretchable elastic fabric panel extending within said attached remaining side edges to be stretched away from said one of said at least two identically cut elastic fabric sheets for inserting padding into said at least a first pocket.

22. A cushion liner as claimed in claim 21, wherein said at least a first pocket extends approximately from said proximal end to said distal end of said liner.

23. A cushion liner as claimed in claim 21, wherein remaining side edges of said at least a first stretchable elastic fabric panel are attached to said side edges of one of said at least two identically cut elastic fabric sheets by sewing or heat fusion.

24. A cushion liner as claimed in claim 21, wherein said cushion liner includes at least a second pocket, said second pocket comprising at least a second stretchable elastic fabric panel having a top edge and remaining side edges and wherein only said remaining side edges of said at least a second stretchable elastic fabric panel are attached to said side edges of another of said at least two identically cut elastic fabric sheets with said second stretchable fabric panel overlying said another of said at least two identically cut elastic fabric sheets, said top edge of said at least a second stretchable elastic fabric panel and portions of said at least a second stretchable elastic fabric panel extending within said attached remaining side edges being unattached to said another of said at least two identically cut elastic fabric sheets, thereby permitting said top edge of said at least a second stretchable elastic fabric panel and portions of said at least a second stretchable elastic fabric panel extending within said attached remaining side edges to be stretched away from said another of said at least two identically cut elastic fabric sheets for inserting padding into said at least a second pocket.

25. A cushion liner as claimed in claim 24, wherein said cushion liner includes at least a third pocket, said third pocket comprising at least a third stretchable elastic fabric panel having a top edge and remaining side edges and having only said remaining side edges attached to said at least a first stretchable elastic fabric panel with said third stretchable elastic fabric panel overlying said first stretchable elastic fabric panel and with said top edge of said at least a third stretchable elastic fabric panel and portions of said at least a third stretchable elastic fabric panel extending within said attached remaining side edges being unattached to said at least a first stretchable elastic fabric panel, or having only said remaining side edges attached to said at least a second stretchable elastic fabric panel with said third stretchable elastic fabric panel overlying said second stretchable elastic fabric panel and with portions of said at least a third stretchable elastic fabric panel extending within said attached remaining side edges being unattached to said at least a second stretchable elastic fabric panel, thereby forming at least a third pocket overlapping said at least a first pocket or said at least a second pocket, thereby permitting said top edge of said at least a third stretchable elastic fabric panel and portions of said at least a third stretchable elastic fabric panel extending within said attached remaining side edges to be stretched away from said at least a first pocket or said at least a second pocket for inserting padding into said at least a third pocket.

26. A cushion liner as claimed in claim 25, wherein both said at least a third pocket and said overlapped first pocket or second pocket extend approximately from said proximal end to said distal end of said liner.

27. A cushion liner as claimed in claim 26, wherein said liner includes padding disposed in at least one of said pockets.

28. A cushion liner as claimed in claim 27, wherein said padding is a foam-type for comfort, a pneumatic-type for comfort, a heating-type for heat therapy or a pressure sensing type for sensing pressure points.

29. A cushion liner as claimed in claim 25, wherein said at least two identically cut elastic fabric sheets and each of said elastic stretchable fabric panels are of the same material or of different materials.

30. A cushion liner as claimed in claim 29, wherein said at least two identically cut elastic fabric and each of said elastic stretchable fabric panels are polyester, rayon, nylon, or any combination thereof.

31. A cushion liner as claimed in claim 25, wherein said at least two identically cut elastic fabric sheets and each of said stretchable elastic fabric panels have a longitudinal stretch of 5% to 180% and a transverse stretch of 50% to 250%.

32. A cushion liner as claimed in claim 25, wherein said at least two identically cut elastic fabric sheets and each of said stretchable elastic fabric panels have a thickness of between 0.30 mm and 1.5 mm.

33. A cushion liner as claimed in claim 25, wherein said remaining side edges of said at least a third stretchable elastic fabric panel are attached to said side edges of said at least a first or second stretchable elastic fabric panel by sewing or heat fusion.

34. A cushion liner as claimed in claim 24, wherein said at least a second pocket extends approximately from said proximal end to said distal end of said liner.

35. A cushion liner as claimed in claim 24, wherein said remaining side edges of said at least a second stretchable elastic fabric panel are attached to said side edges of another of said at least two identically cut elastic fabric sheets by sewing or heat fusion.

36. A cushion liner as claimed in claim 20, wherein said at least a first pocket extends approximately from said proximal end to said distal end of said liner.

37. A cushion liner as claimed in claim 20, wherein said polymeric cushioning material is a thermoplastic triblock copolymer, a copolymer styrene gel or a polyurethane gel.

38. A cushion liner as claimed in claim 20, wherein said liner includes a distal insert attached to the distal end of said liner.

39. A cushion liner as claimed in claim 38, wherein said distal insert is molded into said polymeric cushioning material at the distal end of said liner.

40. A cushion liner as claimed in claim 38, wherein said distal insert attached to the outer surface of said elastic covering at the distal end of said liner.

41. A cushion liner as claimed in claim 1, wherein said outer elastic fabric tubular-shaped covering comprises at least two non-identically cut elastic fabric sheets each having a top edge and side edges wherein said side edges of each sheet are attached together to form said outer elastic fabric tubular-shaped covering having an open proximal end for introduction of said stump and a closed distal end opposite said open end, said at least two non-identically cut elastic fabric sheets each having an outer surface and an inner surface, said inner surfaces coated seamlessly with a polymeric cushioning material that substantially conforms to the shape of said amputation stump when said liner is worn.

42. A cushion liner as claimed in claim 41, wherein said remaining side edges of said at least a first stretchable elastic fabric panel are attached to said side edges of one of said at least two non-identically cut elastic fabric sheets with said first stretchable elastic fabric panel overlying said one of said at least two non-identically cut elastic fabric sheets and with said top edge of said at least a first stretchable elastic fabric panel and portions of said at least a first stretchable elastic fabric panel extending within said attached remaining side edges being unattached to said one of said at least two non-identically cut elastic fabric sheets, thereby permitting said top edge of said at least a first stretchable elastic fabric panel and portions of said at least a first stretchable elastic fabric panel extending within said attached remaining side edges to be stretched away from said one of said at least two non-identically cut elastic fabric sheets for inserting padding into said at least a first pocket.

43. A cushion liner as claimed in claim 42, wherein said at least a first pocket extends approximately from said proximal end to said distal end of said liner.

44. A cushion liner as claimed in claim 42, wherein said side edges of said at least a first stretchable elastic fabric panel are attached to said side edges of one of said at least two non-identically cut elastic fabric sheets by sewing or heat fusion.

45. A cushion liner as claimed in claim 41, wherein said cushion liner includes at least a second pocket, said second pocket comprising at least a second stretchable elastic fabric panel having a top edge and remaining side edges and wherein only said remaining side edges of said at least a second stretchable elastic fabric panel are attached to said side edges of another of said at least two non-identically cut elastic fabric sheets with said second stretchable fabric panel overlying said another of said at least two identically cut elastic fabric sheets, said top edge of said at least a second stretchable elastic fabric panel and portions of said at least a second stretchable elastic fabric panel extending within said attached remaining side edges being unattached to said another of said at least two non-identically cut elastic fabric sheets, thereby permitting said top edge of said at least a second stretchable elastic fabric panel and portions of said at least a second stretchable elastic fabric panel extending within said attached remaining side edges to be stretched away from said another of said at least two non-identically cut elastic fabric sheets for inserting padding into said at least a second pocket.

46. A cushion liner as claimed in claim 45, wherein said cushion liner includes at least a third pocket, said third pocket comprising at least a third stretchable elastic fabric panel having a top edge and remaining side edges and having only said remaining side edges attached to said at least a first stretchable elastic fabric panel with said third stretchable elastic fabric panel overlying said first stretchable elastic fabric panel and with said top edge of said at least a third stretchable elastic fabric panel and portions of said at least a third stretchable elastic fabric panel extending within said attached remaining side edges being unattached to said at least a first stretchable elastic fabric panel, or having only said remaining side edges attached to said at least a second stretchable elastic fabric panel and with portions of said at least a third stretchable elastic fabric panel extending within said attached remaining side edges being unattached to said at least a second stretchable elastic fabric panel, thereby forming at least a third pocket overlapping said at least a first pocket or said at least a second pocket,
    thereby permitting said top edge of said at least a third stretchable elastic fabric panel and portions of said at least a third stretchable elastic fabric panel extending within said attached remaining side edges to be stretched away from said at least a first pocket or said at least a second pocket for inserting padding into said at least a third pocket.

47. A cushion liner as claimed in claim 46, wherein both said at least a third pocket and said overlapped first pocket or second pocket extend approximately from said proximal end to said distal end of said liner.

48. A cushion liner as claimed in claim 46, wherein said at least two non-identically cut elastic fabric sheets and each of said stretchable elastic fabric panels are of the same material or of different materials.

49. A cushion liner as claimed in claim 48, wherein said at least two non-identically cut elastic fabric sheets and each of said stretchable elastic fabric panels are polyester, rayon, nylon, or any combination thereof.

50. A cushion liner as claimed in claim 46, wherein said side edges of said at least a third stretchable elastic fabric panel are attached to said side edges of said at least a first or second stretchable elastic fabric panel by sewing or heat fusion.

51. A cushion liner as claimed in claim 46, wherein said liner includes padding disposed in at least one of said pockets.

52. A cushion liner as claimed in claim 51, wherein said padding is a foam-type for comfort, a pneumatic-type for comfort, a heating-type for heat therapy or a pressure sensing type for sensing pressure points.

53. A cushion liner as claimed in claim 46, wherein said at least two non-identically cut elastic fabric sheets and each of said stretchable elastic fabric panels have a longitudinal stretch of 5% to 180% and a transverse stretch of 50% to 250%.

54. A cushion liner as claimed in claim 46, wherein said at least two non-identically cut elastic fabric sheets and each of said stretchable elastic fabric panels have a thickness of between 0.30 mm and 1.5 mm.

55. A cushion liner as claimed in claim 45, wherein said at least a second pocket extends approximately from said proximal end to said distal end of said liner.

56. A cushion liner as claimed in claim 45, wherein said side edges of said at least a second stretchable elastic fabric panel are attached to said side edges of another of said at least two non-identically cut elastic fabric sheets by sewing or heat fusion.

57. A cushion liner as claimed in claim 41, wherein said at least a first pocket extends approximately from said proximal end to said distal end of said liner.

58. A cushion liner as claimed in claim 41, wherein said polymeric cushioning material is a thermoplastic triblock copolymer, a copolymer styrene gel or a polyurethane gel.

59. A cushion liner as claimed in claim 41, wherein said liner includes a distal insert attached to the distal end of said liner.

60. A cushion liner as claimed in claim 59, wherein said distal insert is molded into said polymeric cushioning material at the distal end of said liner.

61. A cushion liner as claimed in claim 59, wherein said distal insert is attached to the outer surface of said outer elastic fabric tubular-shaped covering at the distal end of said liner.

* * * * *